United States Patent

Rooney et al.

Patent Number: 5,656,014
Date of Patent: *Aug. 12, 1997

[54] ORAL EXAMINATION ILLUMINATING TONGUE DEPRESSOR

[76] Inventors: Christopher F. Rooney, 8300 SW. 8th, Oklahoma City, Okla. 73128; William J. Hale, 35 SE. 33rd, Edmond, Okla. 73013

[*] Notice: The term of this patent shall not extend beyond the expiration date of Pat. No. 5,518,503.

[21] Appl. No.: 600,078

[22] Filed: Feb. 12, 1996

Related U.S. Application Data

[63] Continuation-in-part of Ser. No. 419,496, Apr. 10, 1995, Pat. No. 5,518,503.
[51] Int. Cl.[6] .................... A61B 13/00; A61C 17/10
[52] U.S. Cl. ................................................. 600/240
[58] Field of Search ......................... 600/196, 199, 600/240; D24/136; 606/1, 119, 161, 162, 190, 191

[56] References Cited

U.S. PATENT DOCUMENTS

| 3,638,644 | 2/1972 | Reick . |
| 3,760,798 | 9/1973 | Edinger . |
| 4,807,599 | 2/1989 | Robinson et al. . |
| 4,996,976 | 3/1991 | Nakagawa . |
| 5,518,503 | 5/1996 | Rooney et al. ............ 600/240 |

FOREIGN PATENT DOCUMENTS

| 2191949 | 12/1987 | United Kingdom ............ 600/19 |

*Primary Examiner*—Glenn Dawson
*Attorney, Agent, or Firm*—Robert K. Rhea

[57] ABSTRACT

An illuminated tongue depressor is formed by an elongated relatively narrow body having a handle end portion containing a battery and a proximal end portion having a curvature conforming to the larynx defining a convex top surface and a concave ventral surface having a friction inducing antislip texture adjacent its proximal end. A lamp imbedded in the top surface is connected with the battery by wiring through a switch. A sanitary disposable sheath envelopes the proximal end portion of the body.

3 Claims, 1 Drawing Sheet

U.S. Patent    Aug. 12, 1997    5,656,014
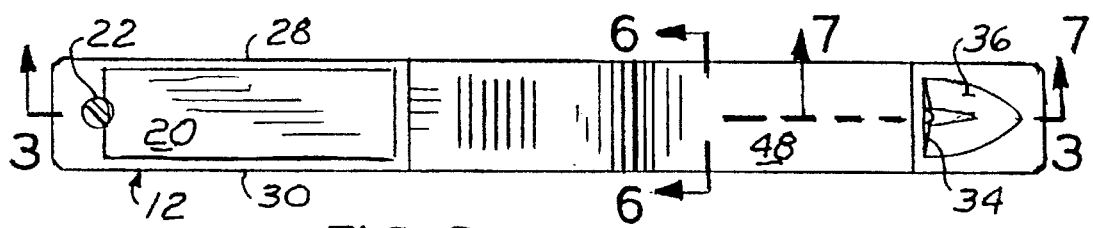
FIG. 2
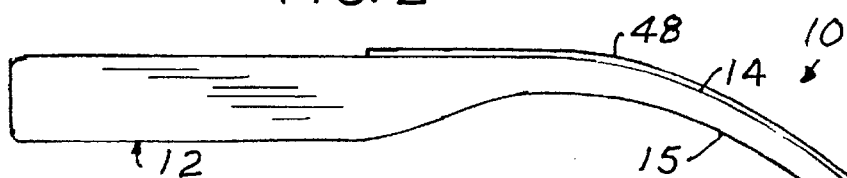
FIG. 1
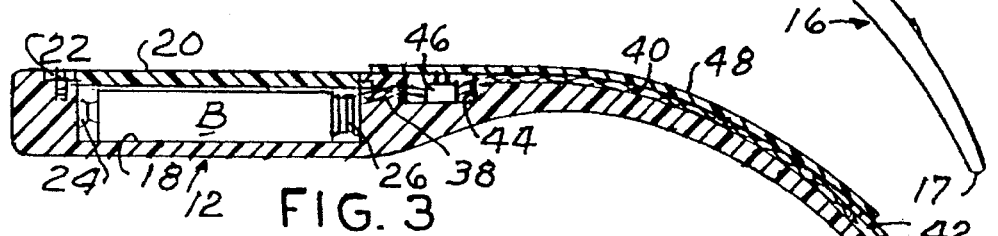
FIG. 3
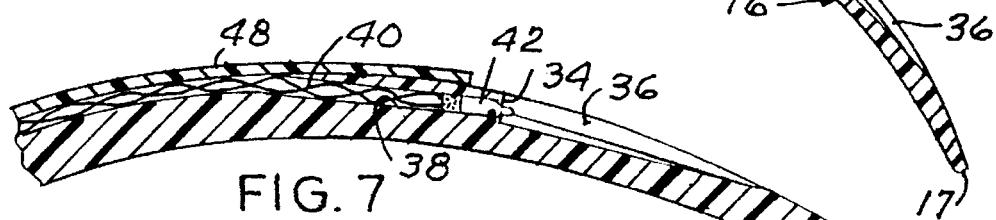
FIG. 7
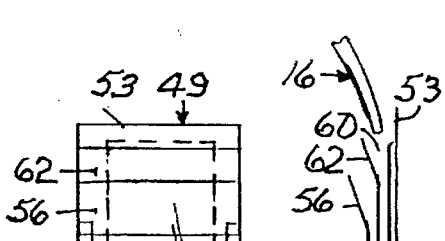
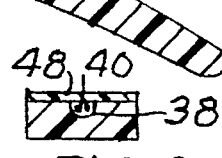
FIG.10  FIG. 6
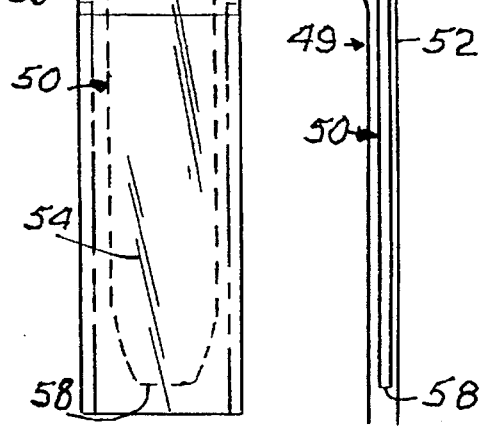
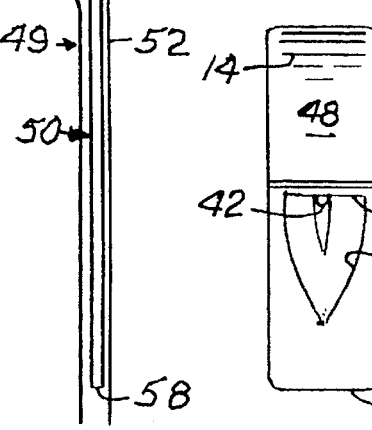
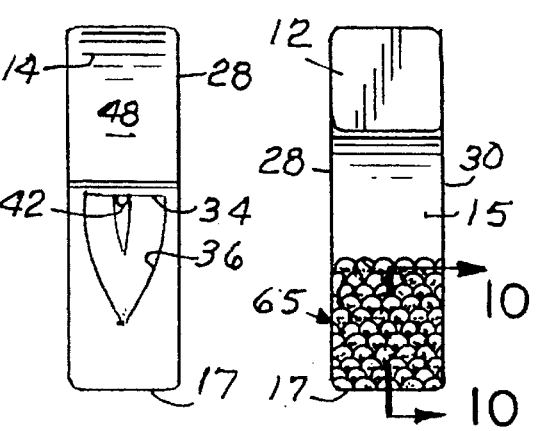
FIG. 8    FIG. 9    FIG. 4    FIG. 5

ORAL EXAMINATION ILLUMINATING TONGUE DEPRESSOR

CROSS REFERENCE TO RELATED APPLICATION

This application is a continuation-in-part of an application filed by us on Apr. 10, 1995 under Ser. No. 08/419,496 for Oral Examination Tongue Depressor, now U.S. Pat. No. 5,518,503.

BACKGROUND OF THE INVENTION

1. Field of the Invention

This invention relates to medical equipment and more particularly to an improvement in a tongue depressor.

Conventional tongue depressors comprise an elongated relatively thin length of material (usually wood) having parallel side edges and part circular end surfaces. The present invention is an improvement over conventional tongue depressors by forming an elongated member having a handle end portion and an arcuate curve in its forward end portion which conforms to the arched tongue of a patient.

2. Description of the Prior Art

Prior art illuminated tongue depressors have generally comprised light conductive synthetic material longitudinally bent blade portions releasably connected with a handle member providing a source of electrical energy for luminous material and illuminating a throat area.

The most pertinent patents are believed to be U.S. Pat. No. 3,638,644 issued Feb. 1, 1972 to Reick for ILLUMINATED SURGICAL SPECULUM, and U.S. Pat. No. 3,760,798 issued Sep. 25, 1973 to Edinger for SELF ILLUMINATING TONGUE DEPRESSOR AND THE LIKE.

The Reick patent *644 discloses a handle battery and lamp container attached to one end of an elongated longitudinally arcuately curved tongue depressor formed from heat resistance material and having an overlying light transmitting strip with its forward end portion dispersing light laterally when illuminated by a bulb.

The Edinger patent *798 similarly discloses a battery and lamp containing handle member which removably receives an elongated angularly bent tongue cleaner depressor which, when inserted at one end into the handle member, energizes the light to shine toward the forward end of the tongue depressor.

More recent patents generally representing the state-of-the-art, are U.S. Pat. No. 4,807,599 issued Feb. 28, 1989 to Robinson, et al for ILLUMINATING TONGUE DEPRESSOR, and U.S. Pat. No. 4,996,976 issued Mar. 5, 1991 to Nakagawa for TONGUE DEPRESSOR WITH ILLUMINATING MEANS. Both of these patents disclose a tongue depressor having a handle end portion provided with illuminating means which illuminates a forwardly extending tongue depressor portion formed from supporting material which transmits and radiates light from the illuminating means in the handle.

This invention is believed distinctive over the above named patents by providing a longitudinally arcuately curved tongue depressor containing a battery in its handle portion energizing a lamp embedded in the top surface of the tongue depressor at its forward end portion in which the light rays from the lamp are directed toward the throat area adjacent the forward end of the tongue depressor.

SUMMARY OF THE INVENTION

The tongue depressor is preferably molded from plastic material and is elongated, relatively narrow and thin at its forward end portion when compared with its straight rearward handle portion and is longitudinally arcuately bowed on a selected radius.

The convex surface of the depressor forms its top surface and its opposite concave surface forms the ventral or bottom surface when in use. A manually closed switch adjacent the handle illuminates a lamp at its forward end portion. Adjacent its forward end the ventral surface is provided with a friction inducing texture preventing lateral movement of the depressor relative to the tongue and pulls the tongue forwardly when pressure is applied to a patient's tongue.

The principal objects of the invention are: to provide a longitudinally arcuately curved tongue depressor having a friction inducing texture on its ventral surface at its forward end portion to provide adhesive action in response to applied pressure; to follow the curve of the oral cavity conforming to and griping a patient's tongue to keep it from buckling; to allow maximum pressure to be applied with minimal deflection and without danger to a patient; provides a total illuminated view of the oro-pharynx and the throat area without touching the back of the throat; and, with less time required and minimal discomfort to the patient.

BRIEF DESCRIPTION OF THE DRAWINGS

FIG. 1 is a side elevational view;

FIG. 2 is top view;

FIG. 3 is a longitudinal cross sectional view taken substantially along the line 3—3 of FIG. 2;

FIG. 4 is a front elevational view;

FIG. 5 is a rear elevational view;

FIG. 6 is a vertical cross sectional view taken substantially along the line 6—6 of FIG. 2;

FIG. 8 is a plan view of a sheath assembly;

FIG. 9 is a diagram; and,

FIG. 10 is a fragmentary vertical cross section, to an enlarged scale taken substantially along the line 10—10 of FIG. 5.

DESCRIPTION OF THE PREFERRED EMBODIMENTS

Like characters of reference designate like parts in those figures of the drawings in which they occur.

In the drawings:

The reference numeral 10 indicates the tongue depressor as a whole formed from plastic material having a uniform width and a selected length defining a body portion having a linear handle section 12 at its distal end portion and a longitudinally arcuately curved forward portion 16 longitudinally bowed on a selected radius defining a convex surface 14 and a concave surface 15 converging toward a substantially strap iron shape at its proximal end 17 which enhances visibility of the mouth and throat area by lowering the position of a physician's hand relative to a patient's mouth while partially conforming to the arch of an extended tongue.

The handle portion 12 is longitudinally and transversely recessed to form a battery compartment 18 normally closed by a cap 20 secured by a fastener 22. The walls forming the end limits of the battery compartment are provided with battery terminal contacts 24 and 26 for operatively receiving a battery B and illuminating a lamp as hereinafter described.

Between its side edges 28 and 30, the forward end portion of the convex top surface 14 is provided with a shallow recess forming a forwardly facing V-shaped wall 34 with the bottom surface of the recess 36 converging forwardly toward the convex surface adjacent the proximal end.

The proximal end portion 16 is provided with a longitudinal bore 38 extending forwardly from the battery compartment 18 though the forwardly facing wall 34 with the intermediate portion of the bore exposed through the convex surface 14 for receiving wires 40 connecting the battery B with a lamp 42 disposed in the bore adjacent the forwardly facing wall 34.

A switch recess 44 spaced forwardly of the battery compartment 18 intersects the bore 38 for receiving a normally open manually closed switch 46 interposed in the wires 40. A relatively thin pliable plate 48 overlies and is bonded to the convex surface 14 between the forward limit of the battery cap 20 and the forwardly facing wall 34.

The bottom surface of the end portion 16 adjacent its end 17 is provided with an abrasive texture 65, fish scale-like in general appearance, formed by semicircular overlapping members when viewed in elevation. The semicircular areas face toward the medial portion of the depressor and are top surface etched away, so that the central portion of the semicircular members form a series of serrations or teeth 66 (FIG. 10) facing toward the depressor central portion. The teeth 66 act in unison to grip the surface of a patients tongue in an adhesive fashion for resisting lateral and longitudinal movement of the depressor relative to the tongue when pressure is manually applied to the distal end of the tongue depressor, when contacting a patient's tongue, in a downward and forward motion by a physician. This results in depressing the rearward end portion of the tongue adjacent the oro-pharynx and provides a full illuminated view of the throat area.

Referring also to FIGS. 8 and 9, the reference numeral 49 indicates a sanitary sheath assembly comprising a transparent plastic sterile sheath 50 contoured and dimensioned to surround the depressor 10 from its proximal end 17 to its distal end portion 12. The sheath 50 is heat sealed between an opaque back cover 52, having a pull tab 53 at one end, and a transparent front cover 54, similarly having a pull tab 56 at one end. The front and back covers are sealed together along opposing marginal edge portions laterally of the sheath 50.

The sheath 50 is tubular having one closed end 58 and an opposite open end, as at 60, with a portion of its peripheral open end edge sealed to the back cover tab 5∝and the opposite portion of its open end edge bonded to a pull tab 62 of equal width respect to the width of the back cover. The sheath 50 is placed in encompassing relation on the depressor proximal end portion 16 by inserting the proximal end 17 into the open end 60 of the sheath 50 (FIG. 9) and separating the sheath from the front and back covers by manually pulling the front cover tab 56 toward the opposite end of the sheath assembly. The depressor is completely inserted into the sheath 50 by grasping the pull tab 62 and separating the sheath from the back opaque cover pull tab 53.

The sheath assemblies are manufactured in elongated sheet configuration in which the individual sheath assemblies 50 are disposed in juxtaposed relation with only a portion of their marginal side edges joined in breakaway contact from an adjacent sheath assembly.

Operation

In operation, the depressor 10 is manually inserted into a sheath 50, as described hereinabove, and its proximal end portion is inserted into a patient's larynx by the operator grasping the handle portion 12 and pressing, as by a finger or thumb, on the cover plate 48 switch position to energize the lamp 42. Following the oral examination, the user separates the sheath 50 from the depressor 10 and discards the sheath.

Obviously the invention is susceptible to changes or alterations without defeating its practicability. Therefore, we do not wish to be confined to the preferred embodiment shown in the drawings and described herein.

We claim:

1. An illuminated tongue depressor, comprising:

an elongated unitary body relatively narrow when compared with its length defining a handle having a battery compartment and a battery therein at a distal end portion of said body and a depressor blade proximal end portion, said blade having a curvature to facilitate entry into the larynx of a patient and defining a convex top surface and a concave ventral surface converging proximally from the handle;

a friction inducing fish scale-like texture on the ventral surface adjacent a proximal end of said ventral surface for resisting lateral and outward longitudinal movement of the depressor blade relative to a patient's tongue in response to pressure manually applied to the depressor blade when in use, said blade having a lamp socket open through the convex surface adjacent a proximal end of said convex surface;

a lamp in said lamp socket; and, wiring and switch means operatively connecting said lamp with said battery.

2. The tongue depressor according to claim 1 and further including:

a sanitary disposable transparent sheath for enveloping a portion said tongue depressor from a proximal end; and, front and back peal-away covers attached to said sheath for shielding said sheath.

3. An illuminated tongue depressor, comprising: an elongated unitary body relative narrow when compared with its length defining a handle having a battery compartment and a battery therein at a distal end portion of said body and a depressor blade proximal end portion, said blade having a curvature to facilitate entry into the larynx of a patient and defining a convex top surface and a concave ventral surface converging proximally from the handle;

a friction inducing fish scale-like texture on the ventral surface adjacent a proximal end of said ventral surface for resisting lateral and outward longitudinal movement of the depressor blade relative to a patient's tongue in response to pressure manually applied to the depressor blade when in use, said blade having a lamp socket open through the convex surface adjacent a proximal end of said convex surface, said blade having a longitudinal upwardly open groove in its convex surface communicating with the lamp socket;

a lamp in said lamp socket;

wiring and switch means in the groove operatively connecting said lamp with said battery;

a pliable top plate longitudinally overlying the groove and secured to the convex surface; and, a sanitary disposable transparent sheath enveloping said tongue depressor from a proximal end of said tongue depressor.

* * * * *